United States Patent [19]

Lloyd

[11] Patent Number: 4,617,525

[45] Date of Patent: Oct. 14, 1986

[54] SLEEP POSTURE MONITOR AND ALARM SYSTEM

[76] Inventor: Stephen R. Lloyd, 5642 N. Bernard, Chicago, Ill. 60659

[21] Appl. No.: 574,969

[22] Filed: Jan. 30, 1984

[51] Int. Cl.[4] ............................................. G08B 21/00
[52] U.S. Cl. .................................. 340/573; 128/782
[58] Field of Search ............... 340/575, 573, 686, 689, 340/666, 529; 200/DIG. 2, 61.52; 128/782, 774

[56] References Cited

U.S. PATENT DOCUMENTS

| | | | |
|---|---|---|---|
| 3,614,763 | 10/1971 | Yannuzzi | 340/573 |
| 4,126,856 | 11/1978 | Gray et al. | 340/629 |
| 4,146,885 | 3/1979 | Lawson, Jr. | 340/573 |
| 4,282,412 | 8/1981 | Florin | 200/61.52 |
| 4,320,766 | 3/1982 | Alihanka et al. | 128/782 |
| 4,348,562 | 9/1982 | Florin | 340/573 |

Primary Examiner—Glen R. Swann, III

[57] ABSTRACT

A device for awakening a sleeping person when the sleeping person attempts to sleep in a particular sleep posture includes a sensor, a time-delay circuit, and an alarm or other device for generating a stimulus for awakening the person. The time-delay circuit is designed such that it activates the alarm only when the sensor indicates the person is in the particular sleep posture for a predetermined period of time and also stops the alarm when the person stops sleeping in the particular sleep posture. The device can also be used for monitoring the sleeping person's sleep posture for diagnostic purposes.

17 Claims, 8 Drawing Figures

SLEEP POSTURE MONITOR AND ALARM SYSTEM

BACKGROUND OF THE INVENTION

This invention relates to a device for monitoring sleep posture and the prophylaxis of sleep apnea and snoring in cases wherein these conditions are a function of sleep posture.

Sleep apnea is a medical illness in which patients periodically stop breathing during sleep. An apnea is defined as a period of 10 seconds or greater duration of no respiration. After onset of an apnea episode, sleep typically lightens to the point where breathing resumes, after 10 to 180 seconds, or the patient may wake up. Patients usually remain unaware of their sleep apneas, even though they may awaken as many as several hundred times each night. Episodes of repeated sleep apneas may take up practically the entire night.

Three types of sleep apneas have been identified:

(1) Central apneas are defined by an absence of any respiratory effort.

(2) Obstructive apneas involve a collapse of the upper airway. Respiratory efforts are made, but no air flows through the airway.

(3) Mixed apneas are a combination of the two types.

Sleep apnea can lead to additional medical disorders including:

(1) Elevation of blood pressure during sleep which may lead to essential hypertension during wakefulness as well.

(2) Severe cardiac arrhythmias in association with sleep apnea episodes which may lead to cardiac problems.

(3) Sudden unexplained death during sleep.

(4) Excessive daytime sleepiness, which is often severe enough to interfere with employment, driving, and interpersonal and family relationships.

(5) Heavy snoring associated particularly with obstructive apnea. Indeed obstructive apnea has been found in many heavy snorers who did not complain of any other sleep problem.

(6) Damage to the brain and other internal organs associated with repeated episodes of blood oxygen desaturation.

Sleep apneas of the obstructive type are often a function of sleep posture. For example, the patient who experiences sleep apneas when sleeping on his back may have fewer or no significant apnea episodes when sleeping on his side.

Accordingly, it is a principal object of this invention to provide a device to monitor sleep posture during diagnostic polysomnographic monitoring for sleep apnea.

Another object of this invention is to provide a device for the prophylaxis of particular sleep postures with the goal of preventing or reducing the frequency of obstructive sleep apnea episodes and snoring.

A further object of this invention is to provide a device for training patients to avoid sleeping in particular sleep postures by means of an aversive conditioning paradigm.

SUMMARY OF THE INVENTION

In order to achieve the foregoing and in accordance with purposes of the present invention, a device for monitoring the sleep posture of a sleeping person may comprise:

(1) a sensor to generate a detect signal in response to the sleeping person's adopting a particular sleep posture and (2) a means for monitoring the detect signal for diagnostic purposes.

Preferably, the particular sleep posture to be monitored is that where the patient is lying on his back.

Various types of sensors may be used to detect when the sleeping person adopts a particular sleep posture. For example, one or more pressure sensitive switches might be mounted on the sleeping person's body in such a manner that the sleeping person's adopting a particular sleep posture actuates the switch or switches by compression between the sleeper's body and the surface on which he is sleeping.

Sensor means not wholly attached to the sleeper's body might also be used. For example, photo-detectors mounted above the sleeping person's body might be used in conjunction with infra-red or visible light light emitting diodes (LED's) mounted at specific places on the sleeping person's body. In such a configuration, the detect signal is caused by the response of the photo-detector to differential amounts of infra-red or visible light reaching it as the sleeping person's posture changes alter the orientation of the LED light source or sources.

Preferably, the sensor comprises a position sensitive switch mounted on the sleeping person's body and actuated by gravity, said switch comprising an enclosed chamber having electrically nonconductive walls; a freely moving ball of conductive solid or liquid material smaller in volume than and contained within said chamber; at least two electrodes mounted within said chamber such that placing the chamber in a specific range of orientations causes the ball to fall by gravity into a position to close an electrical circuit across the electrodes, and placing the chamber in orientations outside of said specific range causes the conductive object to fall by gravity into a position to open the electrical circuit across the electrodes; said detect signal being generated by the closing or the opening of said electrical circuit.

In the event that it is desired to avoid monitoring transient sleep postures of short duration as, for example, when the sleeping person lies on his back for a few seconds while rolling from a posture on one side to a posture on the other side of his body, a time-delay circuit may be interposed between the sensor and the monitoring means. Said time-delay circuit would detect the signal from the sensor and begin a timing cycle in response to said signal. Upon completion of the timing cycle, the time-delay circuit would issue an enable output signal of its own to the monitoring means. However, if the detect signal from the sensor were interrupted prior to completion of the timing cycle, the timing cycle would terminate without sending the enable signal to the monitoring means. In this way, the monitoring means would ignore occurrences of the particular sleep posture, when such occurrences were shorter than a specified duration. Preferably the maximum allowed duration of interruption would be 1 second and the duration of a complete timing cycle would be 15 seconds.

It might be anticipated that some types of sensor might fail to provide a continuous signal throughout the duration of the occurrence of the particular sleep posture which the sensor is intended to detect. A two-stage time-delay circuit might be used in conjunction with such a sensor, said two-stage circuit being constructed so as to terminate a timing cycle, as described above, upon interruption of the detect signal where the duration of the interruption is greater than a maximum allowed duration, but to continue the timing cycle upon interruption of the detect signal where the interruption is of shorter duration. Preferably, the need for such two-stage time-delay circuits can be avoided by using sensors which do not produce spurious transient interruptions in the detect signal.

Upon diagnosis of the fact that a patient suffers from sleep apnea and/or snoring, the severity of which is a function of sleep posture, it is desirable to have a means to prevent the patient from sleeping in particular sleep postures (usually a posture on the back) and to train the patient not to sleep in particular sleep postures. These objects may be accomplished by consistently awakening the sleeping person whenever he attempts to sleep in said particular sleep postures. A device for awakening a sleeping person who attempts to sleep in a particular sleep postures may comprise:

(1) a sensor to generate a detect signal in response to the sleeping person's adopting said sleep posture;

(2) a time-delay circuit, coupled to the sensor, which starts a timing cycle in response to the detect signal applied thereto, and which generates an enable signal upon completion of the timing cycle, wherein the timing cycle is terminated without generating an enable signal upon interruption of the detect signal prior to the completion of the timing cycle; and (3) a means of generating an awakening stimulus in response to said enable signal.

The sensor in such a device may be any of the various types described above. The use of the time delay circuit ensures that the patient's sleep will not be disturbed as a result of his being transiently in a detected sleep posture while rolling from one non-detected sleep posture to another non-detected sleep posture. For example, in a preferable configuration, the sensor detects when the sleeping person adopts a posture on his back. The time-delay circuit allows the sleeping person to roll from a posture on one side onto his back and then onto the other side without activating the awakening stimulus.

Various types of awakening stimuli may be used. Preferably an audio oscillator coupled to an audio transducer would produce an auditory stimulus of sufficient intensity to awaken a sleeping person. It has been found that an intermittent (pulse modulated) stimulus of 85 to 100 dB falls within a range of sufficient but safe intensity.

For deaf or hard of hearing persons, special awakening stimuli might be required. These might include electrical stimuli, light stimuli, or vibratory stimuli. Of course, numerous variations are possible within each of these classes.

Preferably, the monitor and alarm functions described above may be usefully combined in the same device. In such a device, switches or electrical connectors will allow for the enabling or disabling of specific functions, and the composite device may be operated as a means for diagnostic monitoring of sleep posture, or as a means for the therapeutic prophylaxis of certain sleep postures, or may be used for both purposes simultaneously.

BRIEF DESCRIPTION OF THE DRAWINGS

These and other features, objects, and advantages of this invention will become more fully evident from the following description thereof by reference to the accompanying drawings, wherein like numerals refer to like parts throughout.

DESCRIPTION OF THE PREFERRED EMBODIMENTS

Figure 1:
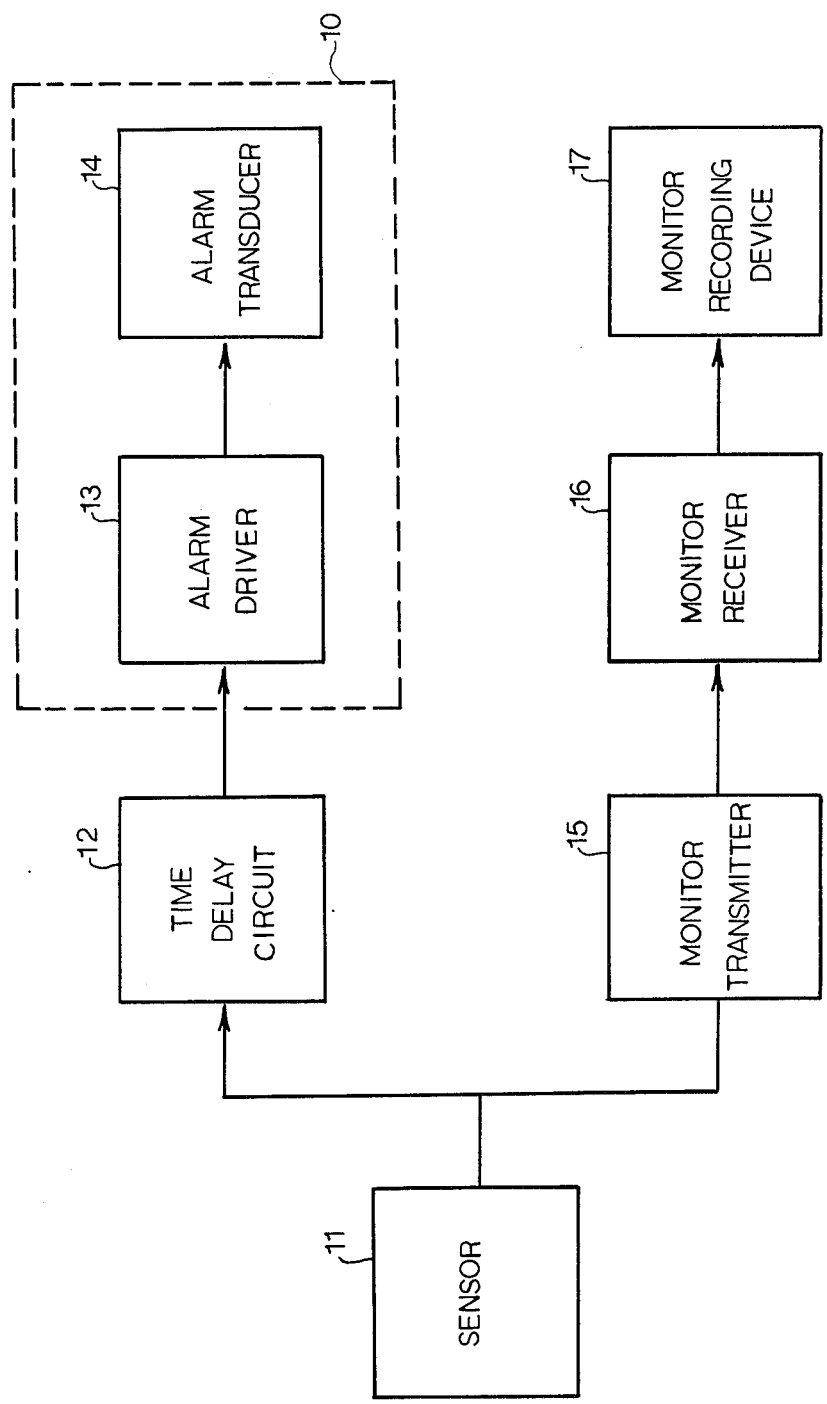
FIG. 1 is a block diagram of the device of this invention.

FIG. 1 is a block diagram of a preferred embodiment of the invention in which sensor 11 detects when the sleeper is lying in a particular sleep posture and sends a signal to time-delay circuit 12 which in turn sends an alarm enabling signal to the alarm driver 13 after the signal from sensor 11 has been present continuously for the specified period of the time delay. Alarm driver 13 and alarm transducer 14 are one example of stimulus generating means 10. If the sleeper ceases to lie in the particular sleep posture during the period of the time delay, the detect signal will cease and the time delay circuit 12 will terminate its timing cycle without sending the alarm enable signal. Once activated, the alarm driver 13 continues to sound the alarm until the sleeper ceases to lie in said particular sleep posture, which, in turn, causes the sensor 11 to cease sending its signal to time-delay circuit 12, which, without delay, stops sending the alarm enabling signal to the alarm driver 13, thus deactivating the alarm driver 13 and the alarm stimulus transducer 14.

Parallel with the above sequence, the sensor 11 also sends a signal to monitor transmitter 15 when the sleeper is lying in the particular sleep posture. Monitor transmitter 15, in turn, sends a signal to the monitor receiver 16. Upon receipt of said signal, the monitor receiver sends an enabling signal to actuate the monitor recording device 17.

Obviously, either of the two sequences 12-13-14 and 15-16-17 can operate independently of the presence or absence of the other.

Figure 2:
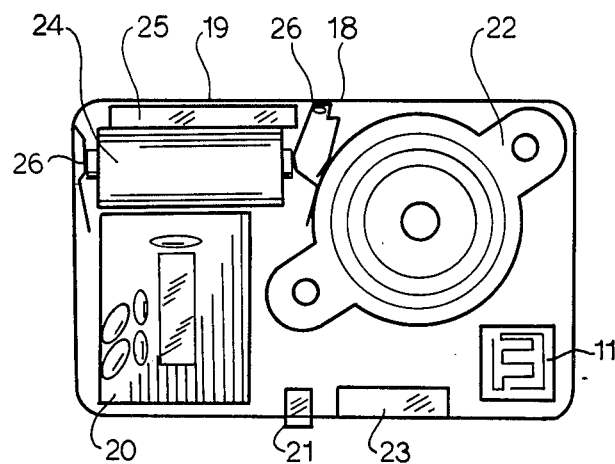
FIG. 2 is a top plan view of the sensor, circuitry, and alarm mounted in a housing.

Referring to FIGS. 2 through 6 and more particularly to FIG. 2, the sensor and alarm device 18 is contained in a housing 19 which is smaller than the size of a cigarette package. Sensor 11 detects when a sleeper is lying on his back by the closing (or opening) of a position-sensitive gravity-actuated switch. When this switch is closed, it starts a timing cycle in a time delay circuit contained within circuit assembly 20. Simultaneously with the onset of this timing cycle, a monitor signal is transmitted from circuit assembly 20 via wires to interface connector 21. Both the timing cycle and the monitor signal are immediately terminated upon the termination of the signal from sensor 11, which will occur if the sleeper ceases to lie on his back. If, however, the timing cycle of the time delay circuit is allowed to run to completion, the time delay circuit sends an enabling signal to the alarm driving circuitry contained partly within the circuit assembly 20 and partly within the piezo-electric buzzer 22, which is a commercially available device comprising a piezo-electric transducer coupled to an audio-frequency oscillator/driver. The alarm function can be turned off by opening switch 23, when this apparatus is to be used for diagnostic monitoring. This apparatus is powered by a small battery 24 which is positioned with the help of spacer 25 to make connection with the battery terminals 26.

Figure 3:
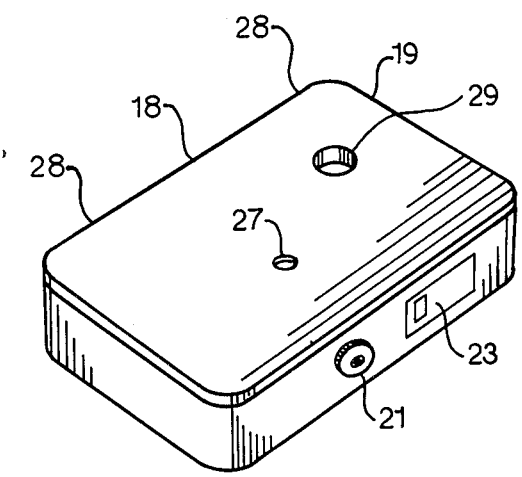
FIG. 3 is a perspective view of the closed housing of FIG. 2.

In FIG. 3, the device 18 is shown contained in a housing 19 which is held closed by screw 27 and hinges 28 (not shown). Orifice 29 allows the piezeo-electric buzzer 22 to be heard at maximum loudness. Monitor interface connector 21 allows for transmission of a signal to an external monitoring device.

Figure 4:
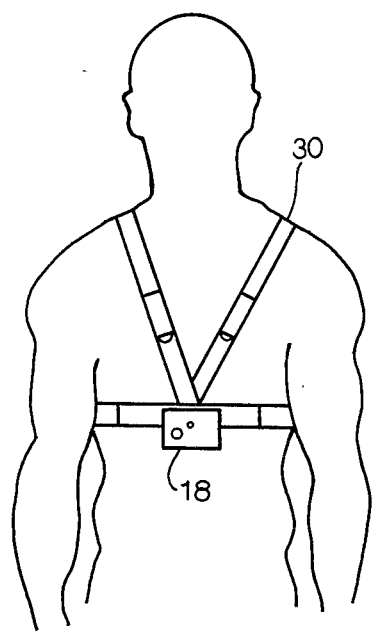
FIG. 4 is a face view of the device of FIGS. 2 and 3 mounted on a patient sleeping on his back.

FIG. 4 shows the device mounted on a patient sleeping on his back by means of an adjustable harness 30, the straps of which can be fastened by Velcro adhesive means.

Figure 5:
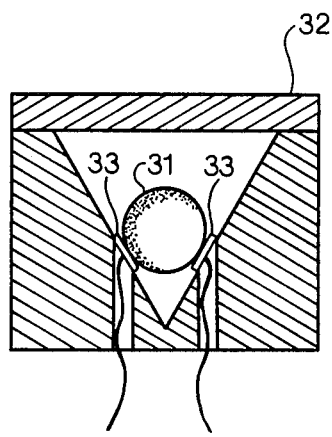
FIG. 5 is a cross section view of a gravity actuated sensor.

FIG. 5 shows a detail of one type of sensor wherein a conductive ball 31 comprised of solid or liquid material is confined within a non-conductive chamber 32, and having electrodes 33 so placed that when the chamber is oriented in a specific position relative to the earth, the conductive ball will roll into the position shown and close the electrical circuit between the electrodes. In other orientations, the conductive ball will roll out of this position and cause a break in the circuit.

Figure 6:
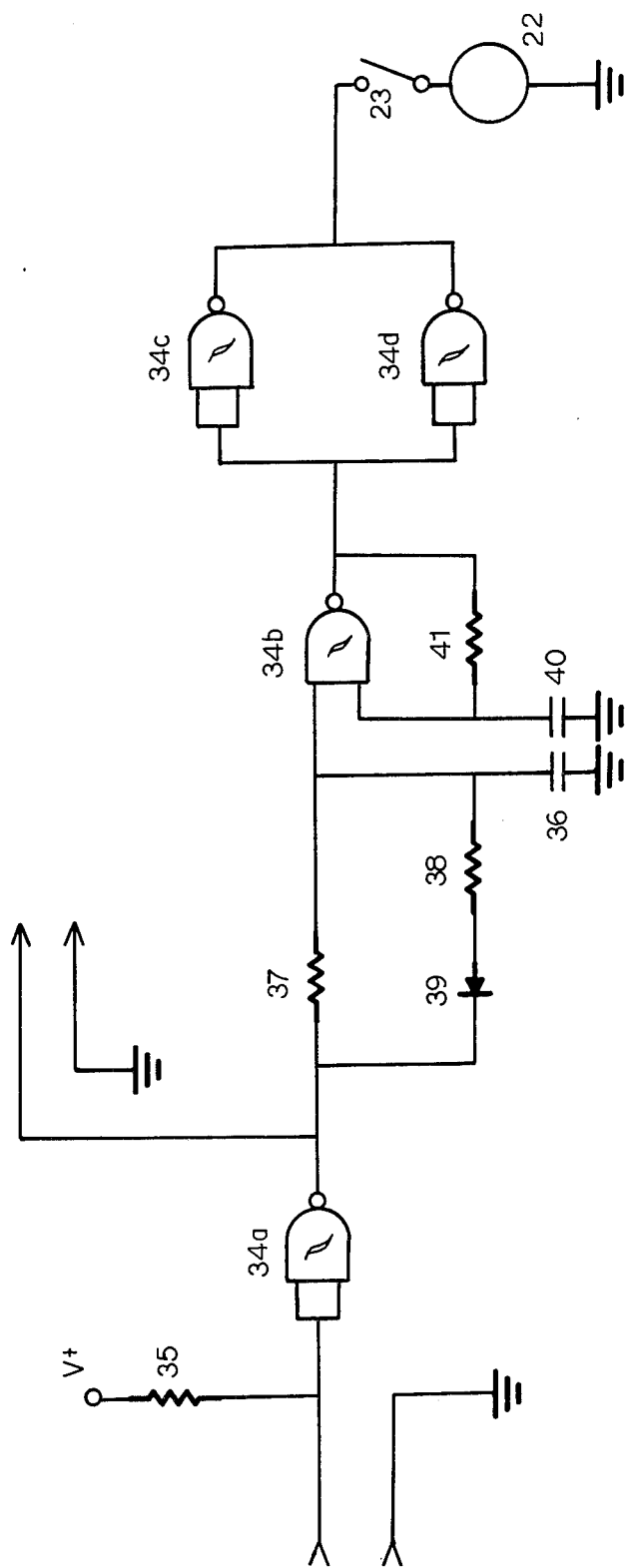
FIG. 6 is an electronic schematic diagram of one of several possible designs to achieve the detect, time-delay, and alarm functions.

FIG. 6 shows an electronic schematic diagram of a circuit assembly which will perform the required functions of circuit assembly 20. The central component of this circuit is a CMOS integrated circuit comprising four NAND Schmitt triggers in a single circuit package. Such integrated circuits are commercially available under the designation CD4093.

In the circuit shown, in its standby state, sensor 11 is an open circuit. Accordingly, the gate inputs of NAND Schmitt trigger gate 34a are held in a high state by pull-up resistor 35. As a result, the inverted output of gate 34a is in a low or ground state and it transmits a zero volt signal to the monitor interface 21. The low output of gate 34a also holds capacitor 36 discharged through resistor 37 and through the series connection of resistor 38 and switching diode 39. Resistor 38 is of comparatively low value, relative to resistor 37 to ensure very rapid discharge of capacitor 36 through this path whenever gate 34a has a low output. Because capacitor 36 is discharged in the standby state, the input of gate 34b to which it is connected is low. Since, if either input of a NAND gate is low, the output is high, the output of gate 34b is high in this standby state. Assuming a sufficiently long period in the standby state, capacitor 40 is fully charged through resistor 41. Because all of the inputs of gates 34c and 34d are held high by the output of gate 34b, their paralleled outputs are low, and no current flows through switch 23 and the piezo-electric buzzer 22.

Closing the circuit of sensor 11 pulls the inputs of gate 34a to ground. This immediately drives its inverted output high, thus transmitting a high signal (V+) to the monitor interface 21. Because the switching diode 39 is reverse biased by the voltage differential between the gate 34a output and the discharged capacitor 36, no current flows along the series pathway 39-38-36. Current flow does occur through resistor 37, however, and capacitor 36 slowing charges through resistor 37. The remainder of the circuitry remains in standby mode until the voltage across capacitor 36 reaches the positive going threshold of the Schmitt trigger gate 34b. Resistor 37, capacitor 36, and one input of the Schmitt trigger gate 34b comprise the time delay circuit shown as box 12 in FIG. 1. If the sensor 11 becomes an open circuit at any time prior to the voltage across capacitor 36 reaching the positive going threshold of gate 34b, then gate 34a will return to its standby state as described above and capacitor 36 will quickly discharge through resistor 38 and diode 39.

Once the positive going threshold of gate 34b is reached by capacitor 36, the time delay is completed and the output of gate 34b is immediately forced low, since its other input has been held high by fully charged capacitor 40 while in the standby mode. When the output of gate 34b goes low, it causes the outputs of gates 34c and 34d to go high, which in turn causes current to flow through switch 23 and piezo-electric buzzer 22. Simultaneously, capacitor 40 begins discharging through resistor 41 to the low output of gate 34b. This discharge continues until the voltage across capacitor 40 drops to the negative going threshold of the input of gate 34b to which it is connected. When this threshold is reached, the output of 34b goes to a high state. This, in turn, causes the outputs of gates 34c and 34d to go low, and no current flows through switch 23 and piezo-electric buzzer 22. Simultaneously, capacitor 40 begins charging again through resistor 41. Thus, the combination of capacitor 40, resistor 41, and the output and one input of the Schmitt NAND gate 34b form an astable multivibrator, with output in the form of a square wave. The values of capacitor 40 and resistor 41 are chosen so as to cause the output frequency of the multivibrator to be low (1–3 Hz). This has the effect of pulse modulating the audio frequency output of the piezo-electric buzzer 22. Intermittent audio stimuli, such as this, are more effective in getting the attention of and awakening a sleeping person than is a continuously sounding signal.

Figure 7:
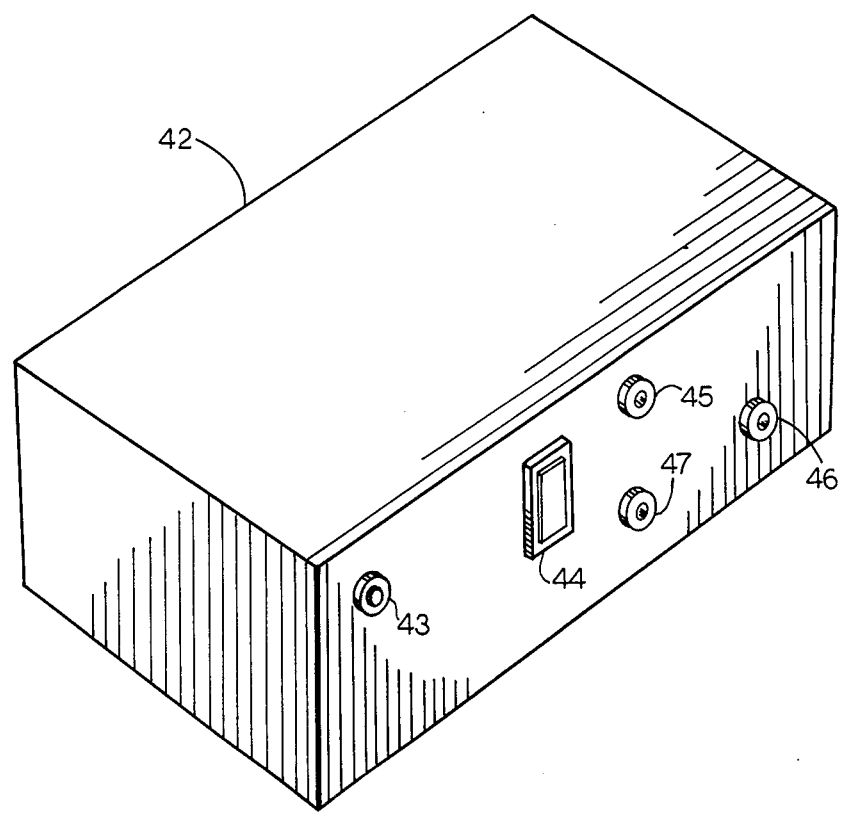
FIG. 7 is a perspective view of a monitor receiver to be connected to the device of FIG. 2.

FIG. 7 is an illustration of one possible monitor receiver device. The device is contained within case 42. Input connector jack 43 is available for a transmission cable connection, the other end of said cable being connected to interface connector 21, shown in FIG. 2. Power switch 44 turns the device's battery power supply on and off. Test button 45 allows the output of the monitor receiver to be tested in the absence of an input signal. Output jacks 46 and 47 provide output signals for use with recording devices such as a polygraph or counting device. The output of jack 46 is the closing of a circuit by means of a relay and thus requires that the recording device provide the activating current. The output of jack 47 is a voltage output provided by the monitor receiver itself. Both outputs are square-wave in form.

Figure 8:
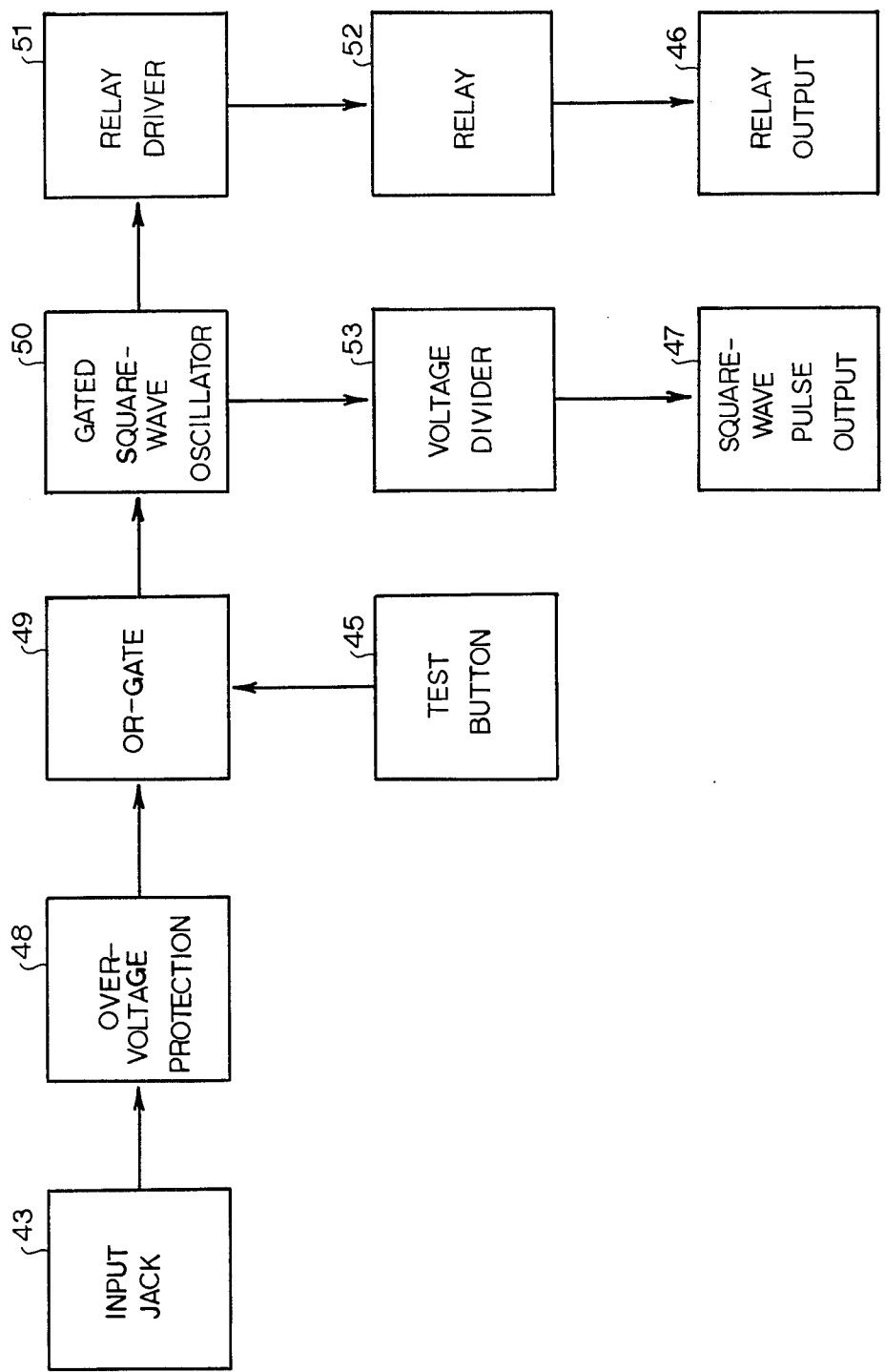
FIG. 8 is a functional block diagram of the circuit assembly of the monitor receiver of FIG. 7.

FIG. 8 is a block diagram for a circuit to perform the functions required for the device illustrated in FIG. 7 and may be regarded as one possible detailed breakdown of block 16 in FIG. 1. Input 43 passes through overvoltage protection circuitry 48. This circuitry protects the remaining circuitry from excessively high input voltages and also allows circuitry associated with the sensor and alarm, shown in FIG. 2, to be operated at higher voltage than the monitor receiver circuitry. The protection circuitry 48 passes the input signal to one input of the OR-gate 49. OR-gate 49 also accepts an input from test button 45. If either the test input or a real input is present, the OR-gate enables low frequency (1–3 Hz) gated square wave oscillator 50. The square wave oscillator intermittently enables relay driver circuitry 51 which provides the higher current necessary to drive the coil of relay 52. As a result, the contacts of relay 52 repeatedly open and close synchronously with the square wave output of oscillator 50. This closure of the relay contacts can be used to control external devices such as the event marker of a polygraph. The output of oscillator 50 also is passed to voltage divider 53 to reduce, if necessary, the voltage output 47 of the square wave to pulses of sufficiently low amplitude to be acceptable to external recording devices such as counting devices or a recording channel of a polygraph.

What is claimed is:

1. A device for monitoring the sleep posture of a sleeping person comprising:
    (a) a sensor to generate a detect signal in response to the sleeping person's adopting a particular sleep posture, said detect signal being terminated upon termination of the person's adopting said particular sleep posture;
    (b) means for monitoring the detect signal for diagnostic purposes;
    (c) a time-delay circuit coupled to said sensor, for generating an enable signal upon completion of a timing cycle in response to the detect signal, wherein the timing cycle is terminated without generating an enable signal upon interruption of the detect signal prior to completion of the timing cycle, wherein the time-delay circuit is constructed so as to terminate a timing cycle upon interruption of the detect signal if the duration of the interruption is greater than a maximum allowed duration and to continue the timing cycle upon interruption of the detect signal if the interruption is of a shorter duration; and
    (d) means for monitoring the enable signal, wherein the enable signal is terminated upon termination of the detect signal.

2. The device of claim 1 wherein said particular sleep posture is on the person's back.

3. The device of claim 1 wherein the sensor comprises a position sensitive switch actuated by gravity, comprising an enclosed chamber having electrically nonconductive walls; a freely movable ball of conductive solid or liquid material smaller in volume than and contained within said chamber; at least two electrodes mounted within said chamber such that placing the chamber in a specific range of orientations causes the conductive ball to fall by gravity into a position to close an electrical circuit across the electrodes, and placing the chamber in orientations outside of said specific range causes the conductive object to fall by gravity into a position to open the electrical circuit across the electrodes; said detect signal being generated by the closing or the opening of said electrical circuit.

4. The device of claim 1 wherein the means for monitoring the detect signal for diagnostic purposes comprises:
    (a) means for transmitting said detect signal to the location of monitoring equipment;
    (b) means for receiving said transmitted detect signal comprising a device capable of generating a monitor signal in response to the transmitted detect signal; and
    (c) means for recording said monitor signal.

5. A device for awakening a sleeping person when the sleeping person attempts to sleep in a particular sleep posture comprising:
    (a) a sensor for generating a detect signal in response to the sleeping person's adopting the sleep posture, wherein said detect signal is terminated upon termination of the person's adopting the sleep posture;
    (b) a time-delay circuit, coupled to said sensor, for generating an enable signal upon completion of a timing cycle in response to said detect signal, wherein the timing cycle is terminated without generating an enable signal upon interruption of the detect signal prior to completion of the timing cycle; and
    (c) means for generating a stimulus for awakening the sleeping person in response to said enable signal, wherein said enable signal is terminated upon termination of said detect signal.

6. The device of claim 5 wherein said particular sleep posture is on the person's back.

7. The device of claim 5 wherein the sensor comprises a position sensitive switch actuated by gravity, comprising an enclosed chamber having electrically nonconductive walls; a freely movable ball of conductive solid or liquid material smaller in volume than and contained within said chamber; at least two electrodes mounted within said chamber such that placing the chamber in a specific range of orientations causes the conductive ball to fall by gravity into a position to close an electrical circuit across the electrodes, and placing the chamber in orientations outside of said specific range causes the conductive object to fall by gravity into a position to open the electrical circuit across the electrodes; said detect signal being generated by the closing or the opening of said electrical circuit.

8. The device of claim 5 further comprising means for monitoring said detect signal.

9. The device of claim 8 further comprising means for monitoring said enable signal.

10. The device of claim 9 further comprising a switch for disengaging said stimulus means.

11. The device of claim 8 wherein the means for monitoring the detect signal comprises:
    (a) means for transmitting said detect signal to the location of monitoring equipment;
    (b) means for receiving said transmitted detect signal comprising a device capable of generating a monitor signal in response to the transmitted detect signal; and
    (c) means for recording said monitor signal.

12. A device for awakening a sleeping person when the sleeping person attempts to sleep in a particular sleep posture comprising:
    (a) a sensor for generating a detect signal in response to the sleeping person's adopting the sleep posture, wherein said detect signal is terminated upon termination of the person's adopting the sleep posture;
    (b) a time-delay circuit, coupled to said sensor, for generating an enable signal upon completion of a timing cycle in response to said detect signal, wherein the timing cycle is terminated without generating an enable signal upon interruption of the detect signal prior to completion of the timing signal; and (c) means for generating a stimulus for awakening the sleeping person in response to said enable signal, wherein said enable signal is terminated upon termination of said detect signal;

(d) wherein said time-delay circuit is constructed so as to terminate a timing cycle upon termination of the detect signal if the duration of said interruption is greater than a maximum allowed duration, and to continue the timing cycle upon interruption of the detect signal if the interruption is of a shorter duration.

13. The device of claim 12 wherein the maximum allowed duration of interruption is 1 second and the duration of a complete timing cycle is 15 seconds.

14. A device for monitoring the sleep posture of a sleeping person comprising:

(a) a sensor for generating a detect signal in response to the sleeping person's adopting a particular sleep posture, wherein sid detect signal is terminated upon termination of the sleeping person's adopting said particular sleep posture;

(b) a time-delay circuit, coupled to said sensor, for generating an enable signal upon completion of a timing cycle in response to said detect signal, wherein said timing cycle is terminated without generating an enable signal upon interruption of said detect signal prior to completion of said timing cycle; and (c) means for monitoring said enable signal, wherein said enable signal is terminated upon termination of said detect signal.

15. The device of claim 14 further comprising means for monitoring said detect signal.

16. The device of claim 14 wherein said particular sleep posture is on the person's back.

17. The device of claim 14 wherein the sensor comprises a position sensitive switch actuated by gravity, comprising an enclosed chamber having electrically nonconductive walls; a freely movable ball of conductive solid or liquid material smaller in volume than and contained within said chamber; at least two electrodes mounted within said chamber such that placing the chamber in a specific range of orientations causes the conductive ball to fall by gravity into a position to close an electrical circuit across the electrodes, and placing the chamber in orientations outside of said specific range causes the conductive object to fall by gravity into a position to open the electrical circuit across the electrodes; said detect signal being generated by the closing or the opening of said electrical circuit.

* * * * *